US011593976B2

(12) United States Patent
Schildkraut et al.

(10) Patent No.: US 11,593,976 B2
(45) Date of Patent: Feb. 28, 2023

(54) SYSTEM FOR THE DETECTION AND DISPLAY OF METAL OBSCURED REGIONS IN CONE BEAM CT

(71) Applicant: Carestream Dental Technology Topco Limited, London (GB)

(72) Inventors: Jay S. Schildkraut, Rochester, NY (US); Krishnamoorthy Subramanyan, Brighton, NY (US)

(*) Notice: Subject to any disclaimer, the term of this patent is extended or adjusted under 35 U.S.C. 154(b) by 0 days.

(21) Appl. No.: 16/476,635

(22) PCT Filed: Jan. 9, 2017

(86) PCT No.: PCT/US2017/012690
§ 371 (c)(1),
(2) Date: Jul. 9, 2019

(87) PCT Pub. No.: WO2018/128630
PCT Pub. Date: Jul. 12, 2018

(65) Prior Publication Data
US 2019/0378310 A1  Dec. 12, 2019

(51) Int. Cl.
*G06T 11/00* (2006.01)
*A61B 6/00* (2006.01)
(52) U.S. Cl.
CPC .......... *G06T 11/005* (2013.01); *G06T 11/006* (2013.01); *G06T 11/008* (2013.01); *A61B 6/4085* (2013.01); *G06T 2211/421* (2013.01); *G06T 2211/436* (2013.01)
(58) Field of Classification Search
CPC .... G06T 11/005; G06T 11/006; G06T 11/008; G06T 2211/421; G06T 2211/436; A61B 6/4085

USPC .................................................. 382/128.131
See application file for complete search history.

(56) References Cited

U.S. PATENT DOCUMENTS

| | | | | |
|---|---|---|---|---|
| 8,565,502 B2* | 10/2013 | Zeng | ...................... | G06T 11/008 382/128 |
| 9,934,597 B2* | 4/2018 | Schildkraut | ........... | G06T 11/005 |
| 2008/0025592 A1* | 1/2008 | Jerebko | .................. | G06T 11/005 382/132 |
| 2011/0044546 A1* | 2/2011 | Pan | ........................ | G06T 11/005 382/195 |

(Continued)

OTHER PUBLICATIONS

Vlasov et al., Few-View Image Reconstruction with SMART and an Allowance for Contrast Structure Shadows, Springer International Publishing Switzerland, 2015, DOI: 10.1007978-3-319-23192-1_56. pp. 667-677 (2015). (Year: 2015).*

(Continued)

*Primary Examiner* — Ishrat I Sherali

(57) ABSTRACT

A method for rendering metal obscured regions in a volume radiographic image reconstructs a first 3D image using a plurality of 2D projection images obtained over a scan angle range relative to the subject and identifies metal in the first 3D image or metal shadows in the plurality of 2D projection images. Then, metal obscured regions are determined in a reconstructed 3D image of the object, and an alternative reconstruction being a limited angle reconstruction is performed for the metal obscured regions and displayed to the user with an indication of the spatial relationship to a corresponding metal obscured region.

15 Claims, 7 Drawing Sheets

(56) References Cited

U.S. PATENT DOCUMENTS

| | | | | |
|---|---|---|---|---|
| 2011/0081071 A1* | 4/2011 | Benson | | A61B 6/5258 |
| | | | | 382/154 |
| 2012/0308101 A1* | 12/2012 | Zeng | | G06T 11/008 |
| | | | | 382/131 |
| 2013/0070991 A1* | 3/2013 | Yang | | G06K 9/00389 |
| | | | | 382/131 |
| 2014/0169650 A1* | 6/2014 | Sakimoto | | A61B 6/03 |
| | | | | 382/131 |
| 2015/0029178 A1* | 1/2015 | Claus | | G06T 11/005 |
| | | | | 345/419 |
| 2015/0228092 A1* | 8/2015 | Claus | | A61B 6/5205 |
| | | | | 382/131 |
| 2016/0078647 A1* | 3/2016 | Schildkraut | | G06T 11/005 |
| | | | | 382/131 |
| 2017/0032546 A1* | 2/2017 | Westerhoff | | G06T 7/0014 |
| 2018/0182128 A1* | 6/2018 | Champley | | G06T 11/003 |

OTHER PUBLICATIONS

Zhang et al., Metal Arifacts Reduction for Tomosynthesis. 2014 IEEE 978-1-4673-1961-4/14, pp. 513-516. (Year: 2014).*

Xu et al., A Metal Projection Segmentation Algorithm Based on Random Walks for Dental CBCT Metal Artifacts Correction. 2013 IEEE 978-1-4799-0534-8/13, pp. 1-4. (Year: 2013).*

Karimi et al., Using Segmentation in CT Metal Artifact Reduction, 2012 IEEE 978-1-4673-1830-3/12, pp. 9-12 (Year: 2012).*

* cited by examiner

SYSTEM FOR THE DETECTION AND DISPLAY OF METAL OBSCURED REGIONS IN CONE BEAM CT

FIELD OF THE INVENTION

This application relates to the field of reconstruction methods of an object that was scanned by a cone beam system that contains metal and other highly attenuating materials, and more particularly to dental imaging apparatus and/or methods for volume reconstruction.

BACKGROUND OF THE INVENTION

Cone beam X-ray scanners are used to produce 3D images of medical and dental patients for the purposes of diagnosis, treatment planning, computer aided surgery, etc. A problem arises when a patent body contains metal and other highly X-ray attenuating materials. Such materials greatly degrade the quality of the reconstructed 3-dimensional (3D) image because of beam hardening, scatter, the exponential edge-gradient effect, aliasing, and/or clipping and the like. Image degradation commonly takes the form of light and dark streaks in soft tissue and dark bands around and between highly attenuating objects. These image degradations are commonly referred to as artifacts because they are a result of the image reconstruction process and only exist in the image, not in the scanned object. The presence of these artifacts not only conceal the true content of the object, but can be mistaken for structures in the object. The reduction of artifacts that are caused by metal and other highly attenuating objects is becoming increasingly important because the use of implants is growing in medical and dental treatments.

Many methods and/or apparatus have been developed to reduce metal artifacts in reconstructions. Most metal artifact reduction (MAR) methods replace the shadow of the metal in the measured projections with 1) interpolated values from the surrounding region or 2) values that were calculated by forward projecting through a prior 3D image. While MAR methods are effective in reducing reconstruction artifacts, MAR generally cannot compensate for the loss of image information caused by obstruction of the X-ray beam by metal. As a result of this information loss, metal obstructed regions in the reconstruction lack detail and are of limited use for the purpose of diagnosis. Unfortunately, it is often the metal obstructed regions that are of highest interest. Indeed, the motivation for acquiring a scan is often to determine that condition of the metal obstructed regions around dental metal implants.

SUMMARY OF THE INVENTION

An aspect of this application is to advance the art of medical dental digital radiography.

Another aspect of this application is to address, in whole or in part, at least the foregoing and other deficiencies in the related art.

It is another aspect of this application to provide, in whole or in part, at least the advantages described herein.

It is another aspect of this application to advance the art of volume imaging and provide improved ways to display to the dentist metal obstructed regions in in CBCT volume images.

An object of this application is to automatically identify metal obstructed regions in a scanned object. It is also an object of this application to determine improved or optimal means to process the measured projections that contain information on these metal obstructed regions. In addition, it is an object of this application to display, in an improved or optimal manner, such metal obstructed region(s) to the user.

The metal obstructed regions generally lack detail in a cone beam CT reconstruction. In accordance with certain exemplary method and/or apparatus embodiments of the application, once such CBCT reconstruction metal obstructed regions are identified, supplemental and alternative non-metal obstructed options for reconstruction and viewing (e.g., limited angle reconstructions or tomosynthesis) are searched for, and when available, provided to the user. For example, when only a small angular range of measured projections contain image information (i.e., non-metal obstructed image information) on a metal obstructed region in the 3D volume reconstruction, these projections can be used to perform a tomosynthesis reconstruction of the region, which is then displayed to the user. When only a single projection image exists (i.e., non-metal obstructed) of the metal obstructed region in the 3D volume reconstruction, this single projection is displayed to the user.

BRIEF DESCRIPTION OF THE DRAWINGS

The foregoing and other objects, features, and advantages of the invention will be apparent from the following more particular description of the embodiments of the invention, as illustrated in the accompanying drawings. The elements of the drawings are not necessarily to scale relative to each other.

DESCRIPTION OF EXEMPLARY EMBODIMENTS

Figure 1:
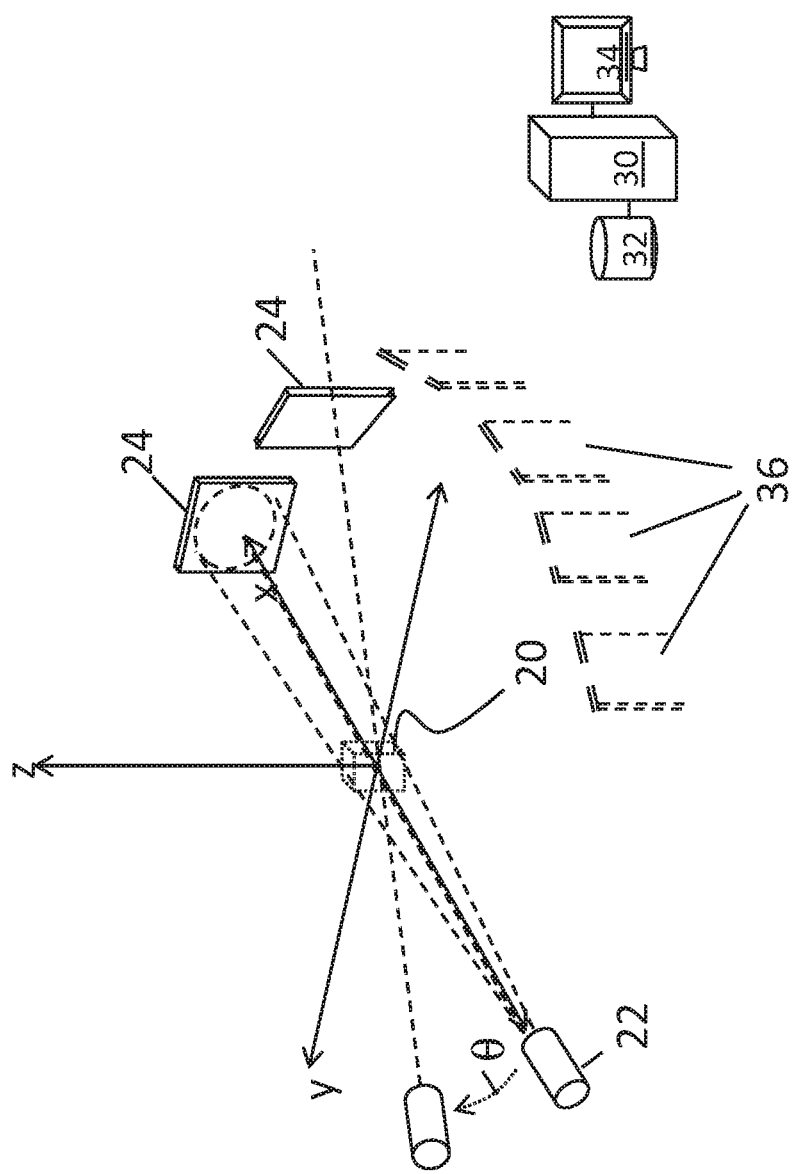
FIG. 1 is a block diagram schematic that shows how projection images are obtained.

The following is a detailed description of exemplary embodiments of the invention, reference being made to the drawings in which the same reference numerals identify the same elements of structure in each of the several figures.

In the drawings and text that follow, like components are designated with like reference numerals, and similar descriptions concerning components and arrangement or interaction of components already described are omitted. Where they are used, the terms "first", "second", and so on, do not necessarily denote any ordinal or priority relation, but are simply used to more clearly distinguish one element from another.

In the context of the present disclosure, the term "volume image" is synonymous with the terms "3-dimensional image" or "3-D image". Embodiments of the present invention are particularly well suited for addressing the types of metal artifacts that occur in 3-D volume images, including cone-beam computed tomography (CBCT) as well as fan-beam CT images.

For the image processing steps described herein, the terms "pixels" for picture image data elements, conventionally used with respect 2-D imaging and image display, and "voxels" for volume image data elements, often used with respect to 3-D imaging, can be used interchangeably. It should be noted that the 3-D volume image is itself synthesized from image data obtained as pixels on a 2-D sensor array and displays as a 2-D image from some angle of view. Thus, 2-D image processing and image analysis techniques can be applied to the 3-D volume image data. In the description that follows, techniques described as operating upon pixels may alternately be described as operating upon the 3-D voxel data that is stored and represented in the form of 2-D pixel data for display. In the same way, techniques that operate upon voxel data can also be described as operating upon pixels.

In the context of the present disclosure, the noun "projection" may be used to mean "projection image", referring to the 2-D image that is captured and used to reconstruct the volume image. In addition, "projection" can also refer to calculated projections for a simulated cone beam system that are obtained by calculating the attenuation of X-rays as they propagate through a 3-D image volume.

An object of exemplary embodiments of the application is to address artifacts in X-ray cone beam reconstructions that are caused by metal and other highly X-ray attenuating materials such as those used for implants that are placed within the body. In the context of the present disclosure, high-density objects that cause what is commonly known as metal artifacts in the volume image are termed "metal" objects. This includes objects formed from materials having a relatively high attenuation coefficient. The attenuation coefficient for a material is not a fixed value, but varies and is dependent, in part, on the photon energy level. An exemplary metal object of titanium, for example, has an attenuation coefficient of about 0.8 cm−1 in the 80 KeV range. Bone has a typical attenuation coefficient of about 0.6 cm−1 in the 80 KeV range. Any object having attenuation at or near that of titanium or higher can be considered to be a metal object. It should be noted, for example, that objects formed from some types of highly dense composite materials can have a similar effect on image quality as objects formed from metal or alloys. The methods of the present invention address the type of artifact generated by such objects, of whatever material type or other composition. Materials commonly used and known to cause at least some type of "metal artifact" in radiographs and volume images include metals such as iron, cobalt, chromium, titanium, tantalum, and alloys including cobalt chromium alloys, for example, as well as some ceramic compositions and various composite materials such as high density composite plastics. Examples of typical implants include various types of prostheses, pins, plates, screws, nails, rods, caps, crowns, bridges, fixtures, braces, dentures, fillings, etc. The implants are usually comprised of metal and/or ceramic material.

CBCT imaging apparatus and the imaging algorithms used to obtain 3-D volume images using such systems are well known in the diagnostic imaging art and are, therefore, not described in detail in the present application. Some exemplary algorithms and approaches for forming 3-D volume images from the source 2-D images, projection images that are obtained in operation of the CBCT imaging apparatus can be found, for example, in the teachings of U.S. Pat. No. 5,999,587 entitled "Method of and System for Cone-Beam Tomography Reconstruction" to Ning et al. and of U.S. Pat. No. 5,270,926 entitled "Method and Apparatus for Reconstructing a Three-Dimensional Computerized Tomography (CT) Image of an Object from Incomplete Cone Beam Data" to Tam.

In typical applications, a computer or other type of dedicated logic processor for obtaining, processing, and storing image data is part of the CBCT system, along with one or more displays for viewing image results. A computer-accessible memory is also provided, which may be a memory storage device used for longer term storage, such as a device using magnetic, optical, or other data storage media. In addition, the computer-accessible memory can comprise an electronic memory such as a random access memory (RAM) that is used for shorter term storage, such as employed to store a computer program having instructions for controlling one or more computers to practice the method according to the present invention.

In order to more fully understand exemplary embodiments of the application and the problems addressed, it is instructive to review principles and terminology used for CBCT image capture and reconstruction. Referring to the perspective view of FIG. 1, there is shown, in schematic form and using enlarged distances for clarity of description, the activity of a conventional CBCT imaging apparatus for obtaining the individual 2-D projection images 36 that are used to form a 3-D volume image. A cone-beam radiation source 22 directs a cone of radiation toward a subject 20, such as a patient or other subject. A sequence of images is obtained in rapid succession at varying projection angles θ about the subject, such as one image at each 1-degree angle increment in a 200-degree orbit. A DR detector 24 is moved to different imaging positions about subject 20 in concert with corresponding movement of radiation source 22. FIG. 1 shows a representative sampling of DR detector 24 positions to illustrate how these images are obtained relative to the position of subject 20. Once the needed 2-D projection images are captured in this sequence, a suitable imaging algorithm, such as filtered back projection (FBP) or other conventional technique, is used for generating the 3-D volume image. Image acquisition and program execution are performed by a computer 30 or by a networked group of computers 30 that are in image data communication with DR detectors 24. Image processing and storage is performed using a computer-accessible memory 32. The 3-D volume image can be presented on a display 34.

FBP is a discrete implementation of an analytic model that assumes that CT transmission measurements are linear functions of the attenuation line integrals along the corresponding primary photon trajectories through the subject and are noiseless. When scanning subjects that comprise anatomically native materials under normal conditions, relatively simple corrections to the raw projection data are sufficient to assure that these assumptions (e.g., linear relationship) are at least approximately true. This treatment allows FBP images that are relatively free of visually observable artifacts. This situation is altered, however, when foreign materials are introduced. In regions shadowed by highly dense, attenuating objects such as metal, there is typically a dramatic increase in noise and nonlinear detector response due to scatter, beam hardening, and photon starvation. This gives rise to pronounced streaking artifacts. Mismatches between the simplified FBP model of detector response and the physical process of signal acquisition when metal objects are in the scanning field of view are the main source of those metal artifacts.

Known MAR methods and/or apparatus are useful to mitigate the metal artifacts based on FBP reconstruction for CBCT acquisitions. Known MAR methods and/or apparatus include MAR image processing in the volume domain, the projection domain or both the volume and projection domains.

However, certain exemplary method and/or apparatus embodiments of this application can provide capabilities for improved visibility for metal obstructed regions in the volume reconstruction of the object. Thus, exemplary embodiments of this application generally can supplement MAR image processing.

Figure 2:
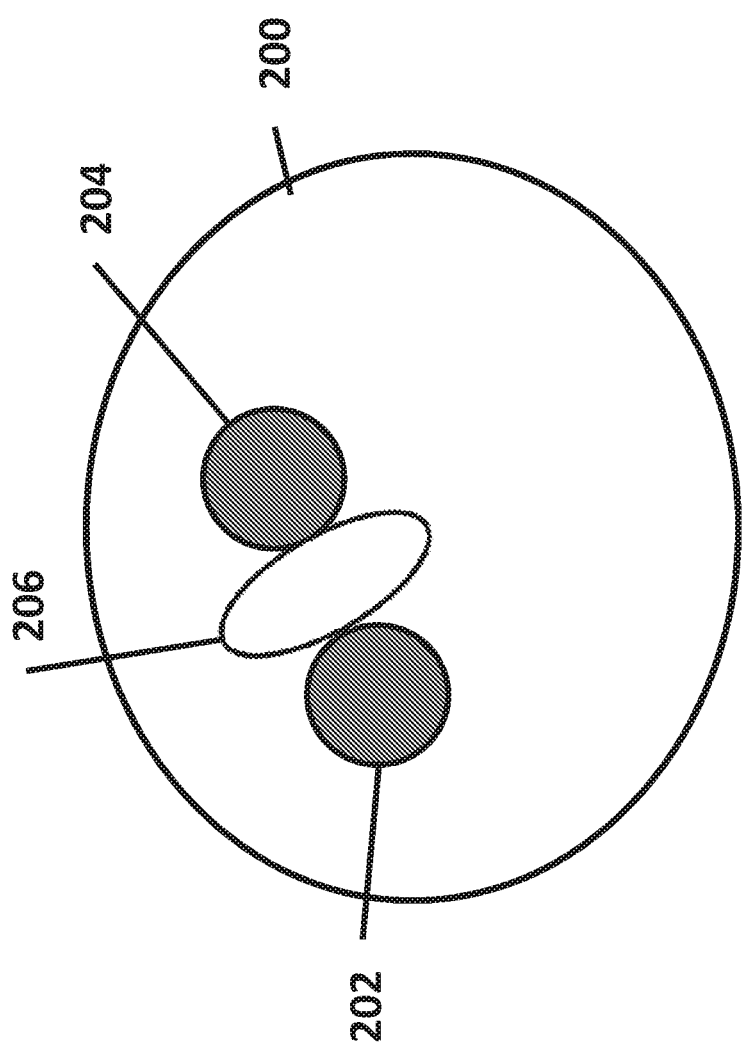
FIG. 2 is a diagram schematic that shows an object that contains two metal regions.

FIG. 2 shows an object 200 that contains two metal regions 202 and 204. The region 206 is substantially obstructed by the two metal regions.

Figure 3:
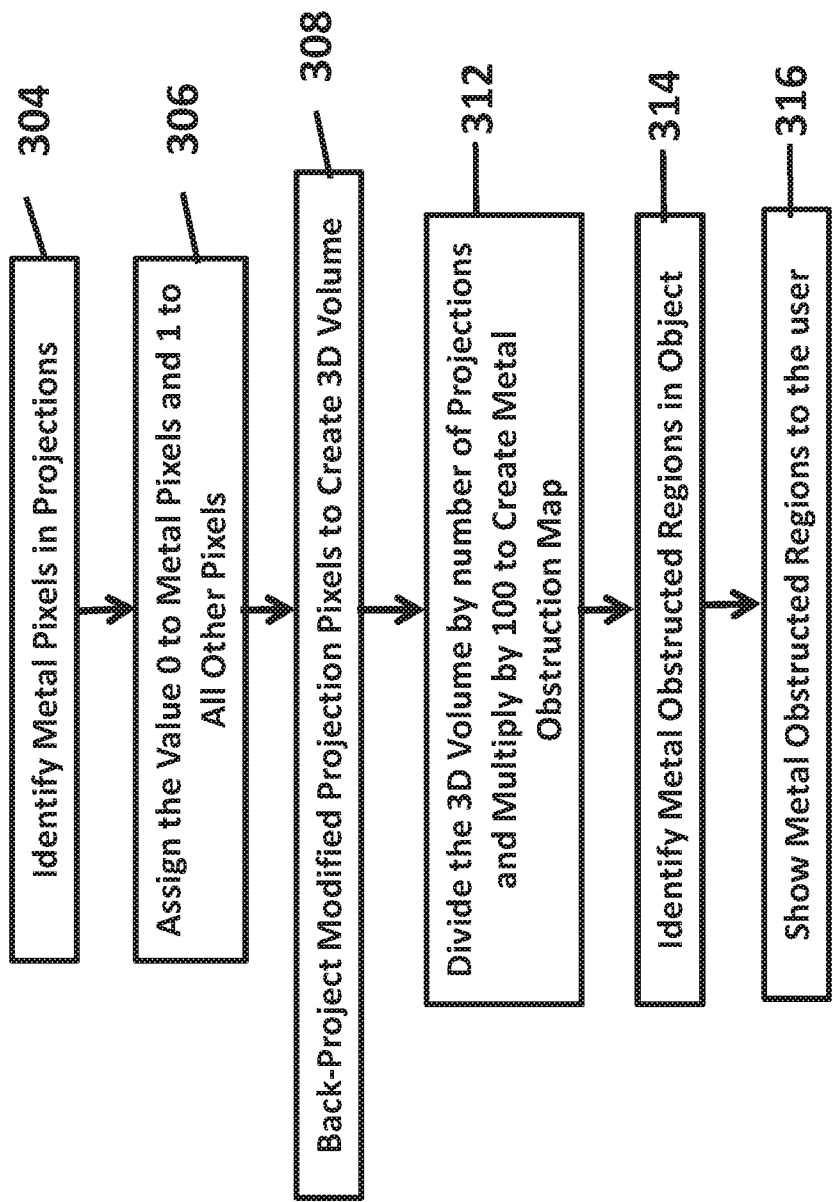
FIG. 3 is a flowchart that shows an exemplary method embodiment according to the application.

FIG. 3 is a flowchart the shows one exemplary method embodiment of this application. As shown in FIG. 3, after the needed sequence of 2D projection images of an object are captured, and optionally, the 3D volume image is generated; pixels of the measured projections that are in the shadow of metal are identified. These metal pixels may be identified by their low X-ray exposure caused by the blockage of the X-rays by metal in the object (block 304). Then, metal pixels are assigned a value of 0.0, and all other projection pixels are assigned a value of 1.0 (block 306). The modified projections are then back-projected to create a 3D volume (block 308). Next, a metal obstruction map can be created for the 3D volume. For example, the 3D volume can be divided by the total number of projections and then multiplied by 100 to create the metal obstruction map (block 312). A value of 100 in the metal obstruction map indicates that a voxel is reconstructed only by non-metal projection pixels, and therefore, that voxel is not obstructed by metal. Non-metal projection pixels are pixels in 2D projection images that are not in the shadow of the metal in the object. Conversely, a value of 0 indicates the voxel is reconstructed only by metal pixels, and therefore, that voxel is completely obstructed by metal. In general terms, the metal obstruction map value of a voxel in the back-projected reconstructed 3D volume is the percentage of pixels with which it is reconstructed that are non-metal. Then, metal obstructed regions can be found (block 314). In one exemplary embodiment, metal obstruction region identification can determine connected 3D regions with a metal obstruction map value below a set threshold. Smoothing of the metal obstruction regions can be performed. Then, metal obstruction regions can be shown to the user (block 316). For example, metal obstruction regions can be shown to the user by being highlighted in the original 3D volume.

Figure 4:
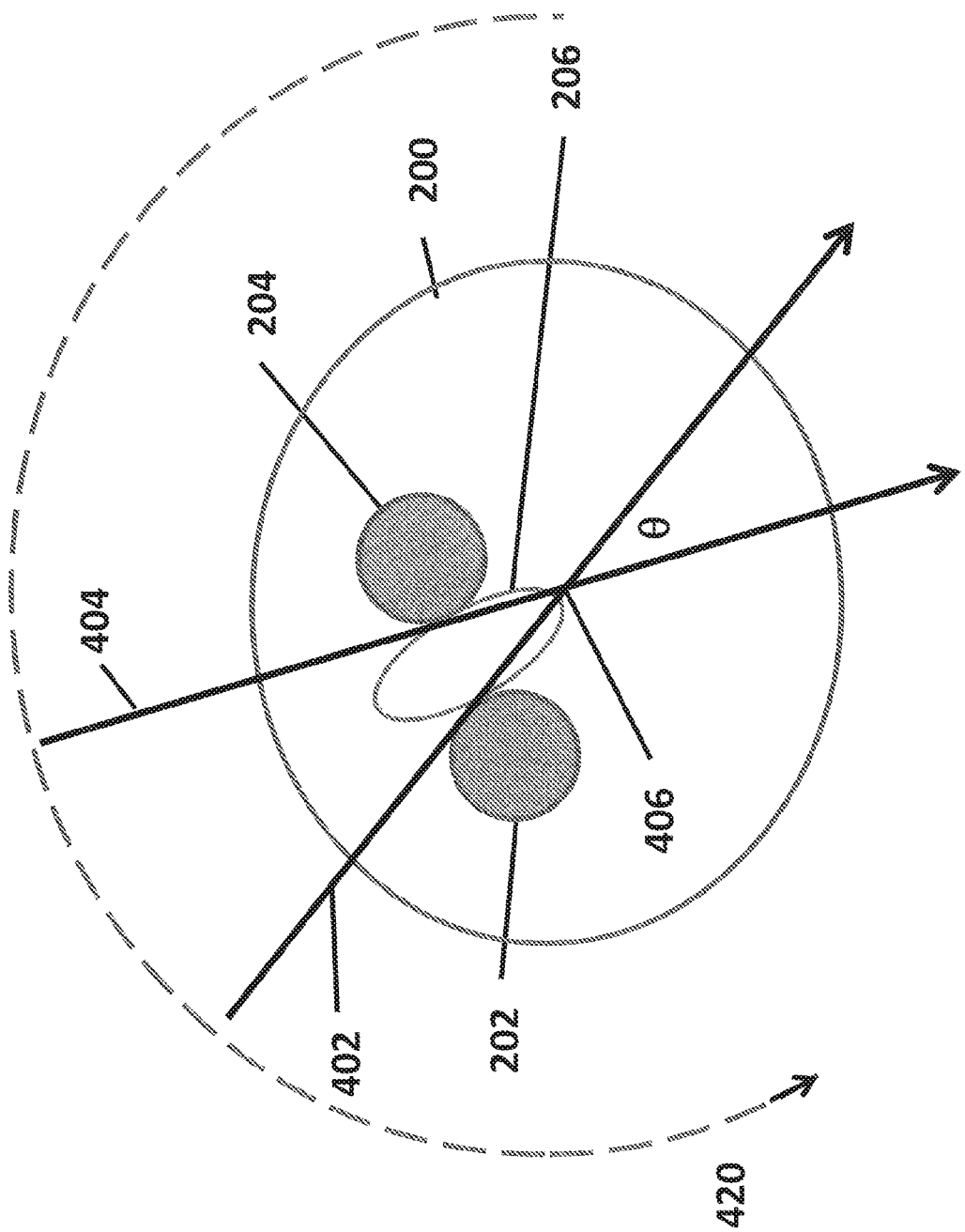
FIG. 4 is a diagram schematic that shows an exemplary alternative characterization for voxels in a metal obstructed region by an angular range of non-metal X-rays that can reconstruct the voxel according to certain method and/or apparatus embodiments of the application.

FIG. 4 is a diagram schematic that shows an exemplary alternative characterization for voxels in a metal obstructed region (e.g., by an angular range of non-metal X-rays that can reconstruct the voxel) according to certain method and/or apparatus embodiments of the application. Non-metal X-rays are X-ray beams or beam paths that do not pass through metal in the object before reaching the detector. As shown in FIG. 4, metal obstructed region 206 is exposed to X-rays which pass through the isocenter 406 with directions between X-ray 402 and 404. The angular range of these rays is denoted by $\Theta$. For a voxel to be properly reconstructed using standard cone beam reconstructed methods $\Theta$ must be at least 180 degrees plus the fan angle of the X-ray beam (e.g., 420). However, many CBCT apparatus use 360 degrees for $\Theta$. If $\Theta$ is less than 180 degrees plus the fan angle of the X-ray beam, because of X-ray blockage by metal, artifacts will occur. Exemplary method and/or apparatus embodiments according to this application can provide an alternative or additional characterization for each voxel in a metal obstructed region by the angular range of non-metal X-rays, which can alternatively reconstruct the voxel.

Figure 5:
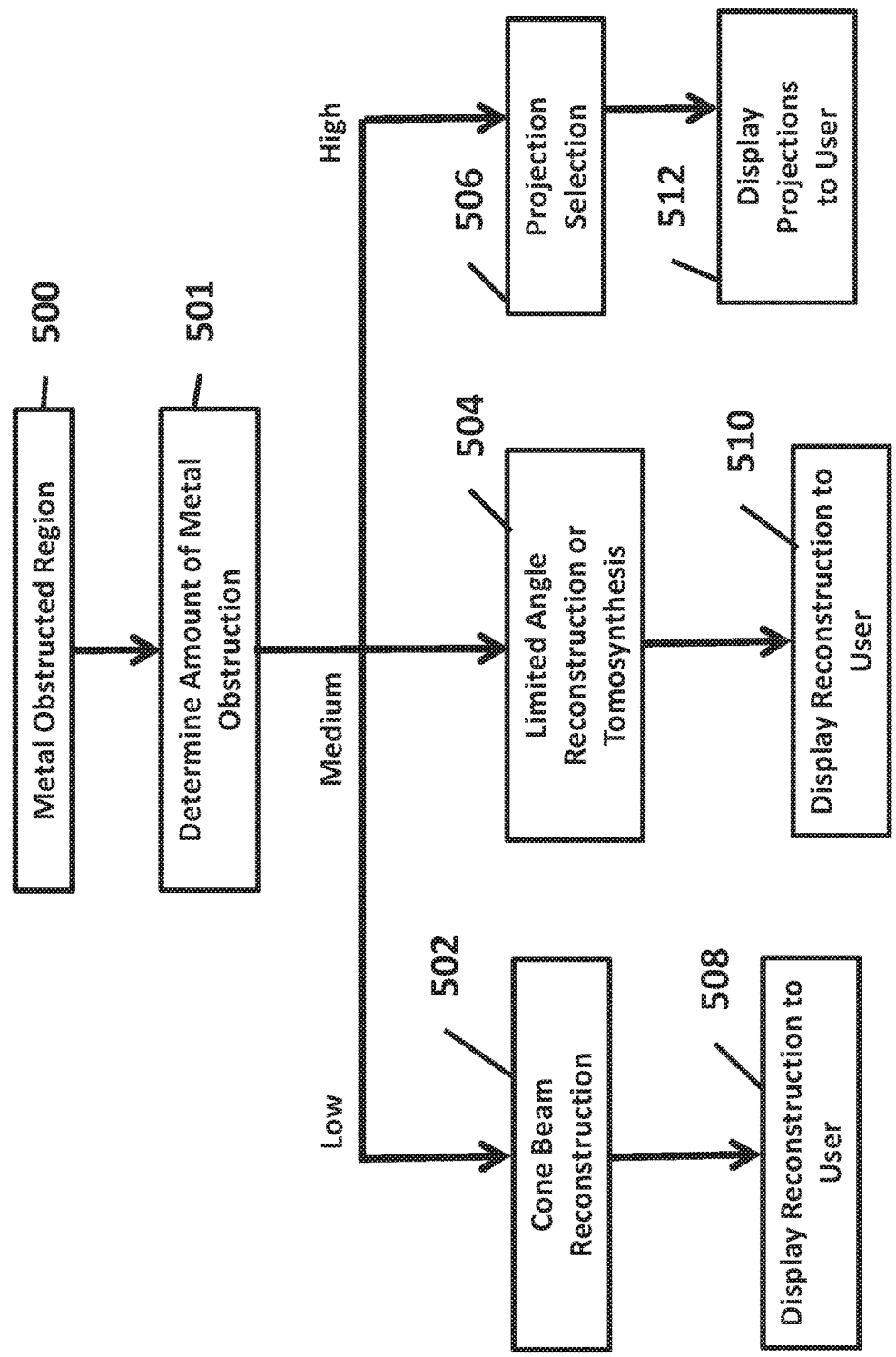
FIG. 5 is a flowchart that shows an exemplary method embodiment according to the application.

As described in FIG. 3, the metal obstruction regions can be shown to the user (e.g., by being highlighted in the original 3D volume). FIG. 5 is a flowchart that shows an exemplary method for showing metal obstruction regions according to the application. As shown in FIG. 5, a metal obstructed region can be automatically identified, for example as described with respect to FIG. 3 (block 500). Alternatively, this region may be a region-of-interest that is specified by a user. Then, the amount of metal obstruction can be determined for the region (block 501). In one exemplary embodiment, the average metal obstruction map value in the region is used as the amount of metal obstruction. If the region's metal obstruction is determined to be low (block 501), a cone beam reconstruction is performed (block 502). Preferably, this is a reconstruction with metal artifact reduction. Then, in block 508, this reconstruction is displayed to the user. In the case of a region that is determined to have a medium amount of metal obstruction (block 501), performing a cone beam reconstruction is counterproductive because many of the measured X-rays that reconstruct the region are completely attenuated by the metal. Hence, the measured value is due to scattered radiation and detector noise. In this case, a limited angle reconstruction or tomosynthesis is performed (block 504), which only uses X-rays that do not pass through metal. For example, a limited angle tomographic reconstruction is performed using lower spatial resolution in the direction of the rays that impinge on the region un-obstructed by metal (e.g., anisotropic voxels), can be performed. Additionally, limited angle reconstructions as described in "Reconstructions in limited angle x-ray tomography: Characterization of classical reconstructions and adapted curvelet sparse regularization," by Jurgen Frikel, Technical University of Munich (2012), which is hereby incorporated by reference in its entirety, can be performed. Then, the limited angle reconstruction or tomosynthesis reconstruction is displayed to the user (block 510). Preferably, the limited angle tomosynthesis reconstruction is displayed with an identified spatial relationship (e.g., visually or text) to the metal obstructed region in the original 3D object reconstruction.

In the case of a region that is determined to have a high amount of metal obstruction (block 501), only a few selected projections, or even a single projection, can have an unobstructed view of the metal obstructed region. In this case, a reconstruction is not possible. Instead, these limited projections (e.g., several or a single projection) are selected (block 506) and displayed to the user in block 512. Preferably, the few selected projections are displayed with an identified spatial relationship (e.g., visually or text) to the metal obstructed region in the original 3D object reconstruction.

In one exemplary embodiment in step 506 overlapping tissue is preferably reduced or removed from the selected projections by performing a cone beam reconstruction and then forward projecting through the volume outside of the metal obstructed region. When this calculated projection is subtracted from a selected projection, the resulting projection will provide a clearer view of the metal obstructed region.

The disclosed exemplary method and/or apparatus embodiments are intended to be non-limiting and other variations are included in the scope of such exemplary embodiments. For example, in block 306 in FIG. 3 instead of assigning a value of 0 to metal pixels and 1 to all other pixels, a value can be assigned which is a function of the metal density in the path of a ray that extends from the X-ray source to the pixel of the detector. Alternatives can be used to identify metal obstructed regions in the object. For example, a reconstruction can be performed and metal voxels in the reconstruction identified. Next, a forward-projection through the reconstruction can identify the shadow of the metal voxels in the projections. Once the metal shadow regions in the projections are determined, these metal shadow regions can be back-projected to determine the regions in the scanned object that are obstructed by metal.

Figure 6:
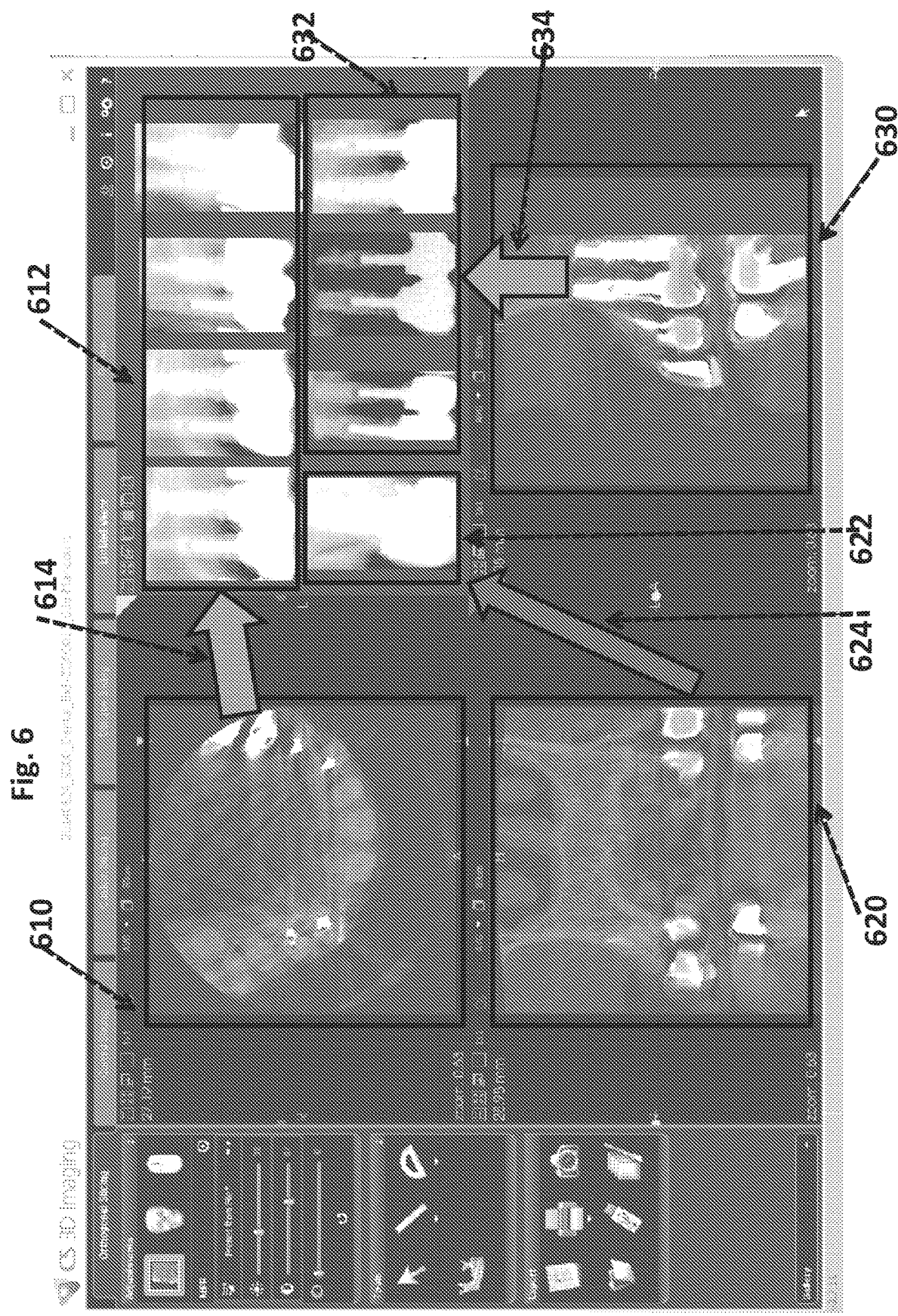
FIG. 6 is a diagram that illustrates a display showing a metal obstructed region in a reconstructed object and at least one alternative display of the metal obstructed region according to one exemplary embodiment of the application.

FIG. 6 is a diagram that illustrates a display showing a metal obstructed region in a reconstructed object and at least one alternative display of the metal obstructed region. As shown in FIG. 6, a 3D volume reconstruction of dentition is shown with an alternative limited angle reconstruction for a corresponding metal obscured region. In FIG. 6, an axial view 610 (or slice), a coronal view 620 (or slice), and a sagittal view 630 (or slice) of a dentition 3D volume reconstruction are shown with corresponding angle reconstructions or tomosynthesis being axial projections 612, coronal projection 622 and sagittal projections 632, respectively. Preferably, an indication is provided to the technician of the spatial relationship between the at least one metal obscured region(s) in a dentition 3D volume reconstruction and the limited angle or tomosynthesis reconstruction. As shown in FIG. 6, visual aids shown as arrows 614, 624 and 634, respectively, visually provide the spatial relationship between the at least one metal obscured region(s) in a dentition 3D volume reconstruction and the limited angle reconstruction or tomosynthesis. However, exemplary embodiments of the application are not intended to be so limited to visual indications for such spatial relationships. As shown in FIG. 6, the display is an exemplary embodiment of a 3D Viewer Layout and Display as known in the dental practice management industry. In such a 3D Viewer Layout and Display, 2D and 3D images can be selected, displayed, manipulated and stored.

Figure 7:
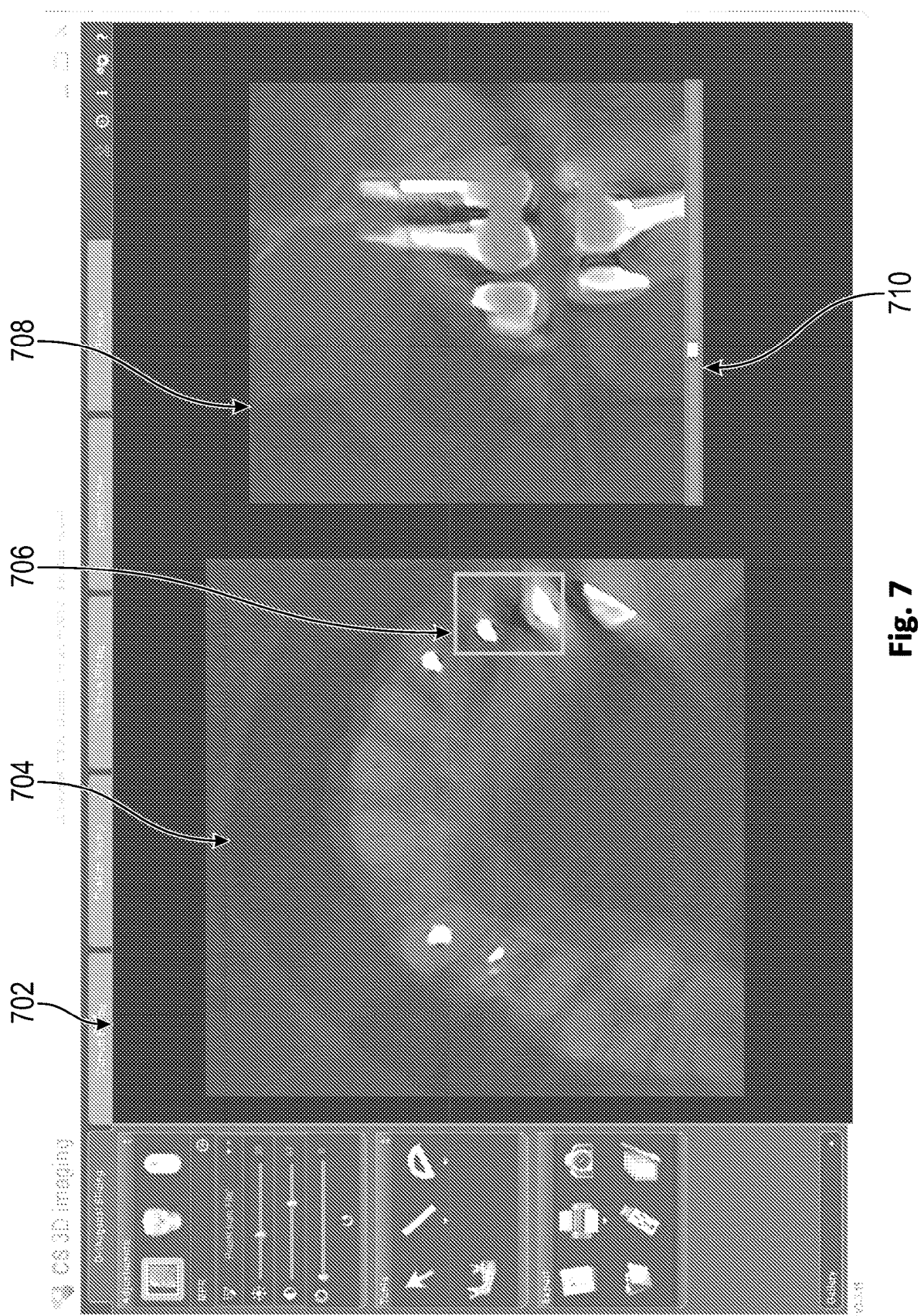
FIG. 7 is a diagram that illustrates a display showing a metal obstructed region in a reconstructed object and at least one alternative display of the metal obstructed region according to another exemplary embodiment of the application.

FIG. 7 illustrates an exemplary embodiment of this application. FIG. 7 is a diagram that illustrates a display showing a metal obstructed region in a reconstructed object and at least one alternative display of the metal obstructed region according to another exemplary embodiment of the application. A window 702 is displayed to the user. In the window a reconstructed axial slice 704 is shown with a region indicted by box 706 which is significantly obstructed by metal. A tomosynthesis reconstruction of this region 708 is displayed to the right of the reconstructed axial slice. Scroll bar 710 provides the user with the ability to scroll through the slices of the tomosynthesis reconstruction. The user is therefore provided with an improved view of the metal obstructed region.

Consistent with exemplary embodiments herein, a computer program can use stored instructions that perform on image data that is accessed from an electronic memory. As can be appreciated by those skilled in the image processing arts, a computer program for operating the imaging system and probe and acquiring image data in exemplary embodiments of the application can be utilized by a suitable, general-purpose computer system operating as control logic processors as described herein, such as a personal computer or workstation. However, many other types of computer systems can be used to execute the computer program of the present invention, including an arrangement of networked processors, for example. The computer program for performing exemplary method embodiments may be stored in a computer readable storage medium. This medium may include, for example; magnetic storage media such as a magnetic disk such as a hard drive or removable device or magnetic tape; optical storage media such as an optical disc, optical tape, or machine readable optical encoding; solid state electronic storage devices such as random access memory (RAM), or read only memory (ROM); or any other physical device or medium employed to store a computer program. Computer programs for performing exemplary method embodiments may also be stored on computer readable storage medium that is connected to the image processor by way of the internet or other network or communication medium. Those skilled in the art will further readily recognize that the equivalent of such a computer program product may also be constructed in hardware.

It should be noted that the term "memory", equivalent to "computer-accessible memory" in the context of the application, can refer to any type of temporary or more enduring data storage workspace used for storing and operating upon image data and accessible to a computer system, including a database, for example. The memory could be non-volatile, using, for example, a long-term storage medium such as magnetic or optical storage. Alternately, the memory could be of a more volatile nature, using an electronic circuit, such as random-access memory (RAM) that is used as a temporary buffer or workspace by a microprocessor or other control logic processor device. Display data, for example, is typically stored in a temporary storage buffer that is directly associated with a display device and is periodically refreshed as needed in order to provide displayed data. This temporary storage buffer is also considered to be a type of memory, as the term is used in the application. Memory is also used as the data workspace for executing and storing intermediate and final results of calculations and other processing. Computer-accessible memory can be volatile, non-volatile, or a hybrid combination of volatile and non-volatile types.

It will be understood that computer program products of the application may make use of various image manipulation algorithms and processes that are well known. It will be further understood that computer program product exemplary embodiments of the application may embody algorithms and processes not specifically shown or described herein that are useful for implementation. Such algorithms and processes may include conventional utilities that are within the ordinary skill of the image processing arts. Additional aspects of such algorithms and systems, and hardware and/or software for producing and otherwise processing the images or co-operating with the computer program product exemplary embodiments of the application, are not specifically shown or described herein and may be selected from such algorithms, systems, hardware, components and elements known in the art.

Certain exemplary method and/or apparatus embodiments according to the application can allow the practitioner to take advantage alternative displays (a limited range of non-obstructed projections for reconstruction and viewing) of metal obscured regions in a 3D volume reconstruction (e.g., CBCT 3D volumes). Preferably, such limited angle (non-obscured) reconstructions or tomosynthesis are displayed to the user with a understandable relationship to a corresponding metal obscured region in the 3D volume reconstruction. Although embodiments of the present disclosure are illustrated using dental imaging apparatus, similar principles can be applied for other types of diagnostic imaging and for other anatomy. Exemplary embodiments according to the application can include various features described herein (individually or in combination).

While the invention has been illustrated with respect to one or more implementations, alterations and/or modifications can be made to the illustrated examples without departing from the spirit and scope of the appended claims. In addition, while a particular feature of the invention can have been disclosed with respect to only one of several implementations/embodiments, such feature can be combined with one or more other features of the other implementations/embodiments as can be desired and advantageous for any given or particular function. The term "at least one of" is used to mean one or more of the listed items can be selected. The term "about" indicates that the value listed can be somewhat altered, as long as the alteration does not result in nonconformance of the process or structure to the illustrated embodiment. Finally, "exemplary" indicates the description is used as an example, rather than implying that it is an ideal. Other embodiments of the invention will be apparent to those skilled in the art from consideration of the specification and practice of the invention disclosed herein. It is intended that the specification and examples be considered as exemplary only, with a true scope and spirit of the invention being indicated by at least the following claims.

The invention claimed is:

1. A method for processing volume image data of a subject, the method executed at least in part on a computer, comprising the steps of:
    scanning a subject to obtain a plurality of 2D radiographic images of the subject on a radiographic detector, where the 2D radiographic images are obtained with the radiographic detector and a radiation source at different scan angles relative to the subject;
    reconstructing the plurality of 2D radiographic images into a 3D volume image reconstruction;
    identifying metal obstructed voxels in the 3D volume image reconstruction;
    identifying one or more metal obstructed regions in the 3D volume image reconstruction from connected ones of the identified metal obstructed voxels;
    after identification of the one or more metal obstructed regions in the 3D volume image reconstruction, simultaneously displaying the 3D volume image reconstruction and at least one additional display of one of the metal obstructed regions, where the at least one additional display is formed by a limited angle technique using a limited subset of the plurality of 2D radiographic images that each include an unobstructed view of the one of the metal obstructed regions, and the at least one additional display is a single projection image, several projection images or a limited angle tomosynthesis reconstruction.

2. The method of claim 1, where the limited angle tomosynthesis reconstruction results in anisotropic reconstructed voxels.

3. The method of claim 1, where the several projection images are less than 5 projection images.

4. The method of claim 1, where the single projection image and the several projection images have overlapping tissue removed.

5. The method of claim 1, where the step of identifying metal obstructed regions in the 3D volume image reconstruction is automatically performed.

6. The method of claim 1, where the single projection image is one of the limited subset of the plurality of 2D radiographic images.

7. The method of claim 1, where the several projection images are ones of the limited subset of the plurality of 2D radiographic images that include 2D radiographic images including an unobstructed view of the metal obstructed region.

8. The method of claim 1, where the step of reconstructing the plurality of 2D radiographic images into a 3D volume image reconstruction uses metal artifact reduction (MAR) in the 3D volume image reconstruction.

9. The method of claim 1, where the limited angle reconstruction technique is a tomosynthesis reconstruction technique.

10. The method of claim 1, where the step of identifying metal voxels in the 3D volume image reconstruction comprises the steps of:
    identifying metal voxels in the 3D volume image reconstruction;
    forward-projecting the identified metal voxels through the 3D volume image reconstruction to generate a second plurality of modified projections in which shadows of the metal voxels can be determined; and
    back-projecting the metal shadow regions in the second plurality of projections to determine one or more regions in the scanned subject that are obstructed by metal.

11. The method of claim 1, where the step of identifying metal obstructed regions in the 3D volume image reconstruction is automatically performed.

12. The method of claim 1, where the first plurality of two-dimensional radiographic images are obtained from a cone-beam computed tomography system or obtained from a fan-beam computed tomography system, and wherein the step of generating the three-dimensional volume image comprises using filtered back projection.

13. The method of claim 1, where the step of simultaneously displaying includes simultaneously displaying the 3D volume image reconstruction, the at least one additional display of one of the metal obstructed regions, and an indication of the spatial relationship therebetween.

14. The method of claim 13, further comprising the step of:
    storing or transmitting the 3D volume image reconstruction, the additional display of one of the metal obstructed regions, and the indication of the spatial relationship therebetween.

15. The method of claim 1, further comprising the step of:
    storing or transmitting the 3D volume image reconstruction and the additional display of one of the metal obstructed regions.

* * * * *